US012310606B2

(12) United States Patent
Corbin et al.

(10) Patent No.: US 12,310,606 B2
(45) Date of Patent: May 27, 2025

(54) APPARATUS AND METHOD FOR TREATMENT OF BOWEL IMPACTION

(71) Applicants: David Corbin, San Diego, CA (US); Aaron Elwyn Christensen, White River Junction, VT (US); Wesley Leuthauser, Lebanon, NH (US)

(72) Inventors: David Corbin, San Diego, CA (US); Aaron Elwyn Christensen, White River Junction, VT (US); Wesley Leuthauser, Lebanon, NH (US)

( * ) Notice: Subject to any disclaimer, the term of this patent is extended or adjusted under 35 U.S.C. 154(b) by 173 days.

(21) Appl. No.: 17/509,998

(22) Filed: Oct. 25, 2021

(65) Prior Publication Data

US 2023/0130710 A1   Apr. 27, 2023

(51) Int. Cl.
*A61B 17/22*   (2006.01)
*A61B 17/28*   (2006.01)

(52) U.S. Cl.
CPC ...... *A61B 17/22031* (2013.01); *A61B 17/282* (2013.01); *A61B 2017/22037* (2013.01)

(58) Field of Classification Search
CPC .......... A61B 2017/22037; A61B 2017/00818; A61B 17/282; A61B 17/28–326; A61B 17/44; A61B 17/50; A61B 2017/505; A61B 2017/22034; A61B 17/22031; A61C 3/10; A61C 3/16; A47J 43/283
USPC ........................................ 606/127; 294/99.2
See application file for complete search history.

(56) References Cited

U.S. PATENT DOCUMENTS

| | | | | |
|---|---|---|---|---|
| 2,644,455 A | * | 7/1953 | Benoit | A61B 17/282 606/205 |
| 4,827,929 A | * | 5/1989 | Hodge | A61B 17/062 606/139 |
| 5,000,750 A | | 3/1991 | Leveen et al. | |
| 5,730,726 A | | 3/1998 | Klingenstein | |
| 7,287,791 B2 | * | 10/2007 | Carolina | B25B 9/02 294/902 |
| 8,105,335 B1 | | 1/2012 | Bentley | |
| 10,166,016 B2 | | 1/2019 | Shimizu et al. | |

(Continued)

FOREIGN PATENT DOCUMENTS

| | | |
|---|---|---|
| CN | 110037770 A | 7/2019 |
| DE | 10 2012 016 439 A1 | 5/2014 |

(Continued)

*Primary Examiner* — Kathleen S Holwerda
*Assistant Examiner* — Serenity A Miller
(74) *Attorney, Agent, or Firm* — Alston & Bird LLP

(57) ABSTRACT

Embodiments of the present disclosure relate to an apparatus and method for treating a bowel obstruction. An example apparatus includes a first tong element and a second tong element forming a pair of tong elements pivotally connected at a junction point and movable between an opened position and a closed position. Each tong element defines a distal end and a proximal end and a body extending therebetween. The distal end of the first tong element defines a first collection half element and the distal end of the second tong element defines a second collection half element. The first collection half element and the second collection half element form a collection element when the pair of tong elements are in the closed position, which defines an inwardly facing cavity. At least one of an interior of the first collection half element or an interior of the second collection half element define a plurality of grasping teeth.

17 Claims, 9 Drawing Sheets

(56) References Cited

U.S. PATENT DOCUMENTS

| | | | |
|---|---|---|---|
| 10,285,717 B2 | 5/2019 | Anderson | |
| 10,413,643 B2 | 9/2019 | Pigazzi | |
| 2004/0024319 A1* | 2/2004 | Flipo | A61B 10/06 |
| | | | 600/459 |
| 2010/0114154 A1* | 5/2010 | Snell | A61B 17/8866 |
| | | | 606/205 |
| 2015/0351784 A1* | 12/2015 | Dao | A61B 17/285 |
| | | | 606/127 |
| 2016/0296274 A1* | 10/2016 | Mensch | A61B 18/1447 |
| 2016/0331408 A1* | 11/2016 | Benson | A61B 17/4241 |
| 2020/0229832 A1* | 7/2020 | Recanati | A61B 17/282 |
| 2020/0281382 A1* | 9/2020 | Siskindovich | A47J 43/283 |
| 2020/0305908 A1* | 10/2020 | Holton | A61B 17/2833 |

FOREIGN PATENT DOCUMENTS

| | | | | |
|---|---|---|---|---|
| KR | 20140012835 A | * | 7/2012 | A61B 17/22 |
| WO | WO 2018/210694 A1 | | 11/2018 | |

* cited by examiner

APPARATUS AND METHOD FOR TREATMENT OF BOWEL IMPACTION

TECHNOLOGICAL FIELD

The present invention relates generally to an apparatus and method and, in particular, to an apparatus and method for treatment of a bowel impaction.

BACKGROUND

Within clinical settings, patients may present with bowel obstructions that require medical intervention. For example, a fecal impaction is a common cause of lower gastrointestinal tract obstructions that may require medical intervention to prevent further issues such as stercoral ulcers, bowel perforations, and peritonitis. Such bowel obstructions may occur for a variety of reasons, including as a side effect from certain prescription and/or over-the-counter medications, particularly those with anticholinergic properties or those which use stimulant laxatives. Additionally, certain populations, such as incapacitated and/or institutionalized elderly patients, individuals (e.g., soldiers) whose food intake involves dehydrated meals ready to eat (MREs), individuals (e.g., astronauts) subjected to extreme arid environmental conditions, and individuals (e.g., distance runners) who partake in high intensity and extreme endurance physical activities are at increased risk for developing bowel obstructions which require medical intervention.

BRIEF SUMMARY

Embodiments of the present disclosure relate to an apparatus and method for treatment of a bowel impaction.

Embodiments provided herein include an apparatus including: a first tong element and a second tong element forming a pair of tong elements, the pair of tong elements pivotally connected at a junction point and movable between an opened position and a closed position; each tong element defining a distal end and a proximal end and a body extending therebetween; the distal end of the first tong element defining a first collection half element and the distal end of the second tong element defining a second collection half element, wherein (i) the first collection half element and the second collection half element form a collection element when the pair of tong elements are in the closed position, (ii) the collection element defining an inwardly facing cavity, and (iii) at least one of an interior of the first collection half element or an interior of the second collection half element define a plurality of grasping teeth.

Embodiments provided herein further include a method for treatment of a bowel impaction including: inserting an apparatus into a patient's rectum, said apparatus comprising: a first tong element and a second tong element forming a pair of tong elements, the pair of tong elements pivotally connected at a junction point and movable between an opened position and a closed position; each tong element defining a distal end and a proximal end and a body extending therebetween; and the distal end of the first tong element defining a first collection half element and the distal end of the second tong element defining a second collection half element, wherein (i) the first collection half element and the second collection half element form a collection element when the pair of tong elements are in the closed position, (ii) the collection element defining an inwardly facing cavity, and (iii) at least one of an interior of the first collection half element or an interior of the second collection half element define a plurality of grasping teeth; actuating the pair of tong elements into the opened position and further advancing the pair of tong elements into the patient's rectum such that at least a portion of the bowel obstruction is encapsulated between the first collection half element and the second collection half element; actuating the pair of tong elements into the closed position to encapsulate at least a portion of the bowel obstruction within the collection element; and removing the apparatus from the patient's rectum.

BRIEF DESCRIPTION OF THE DRAWINGS

Reference will now be made to the accompanying drawings, which are not necessarily drawn to scale, and wherein.

DETAILED DESCRIPTION

The present invention will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

The terms "illustrative" and "exemplary" are used to be examples with no indication of quality level. As used herein, the terms "approximately," "generally," and "substantially" refer to within manufacturing and/or engineering design tolerances for the corresponding materials and/or elements as would be understood by the person of ordinary skill in the art, unless otherwise indicated.

Conventional clinic practices dictate the manual removal of bowel impactions, such as by the insertion of a medical practitioners gloved hand into a patient's rectum to perturb and break-up the bowel obstruction, for instance, when the bowel obstruction is a fecal impaction. While certain medical devices may be used to treat a bowel impaction, such medical devices are often cumbersome to use, require significant training to successfully use, or may be impractical for long-term use for sanitary reasons. Furthermore, some medical devices require fully or partial sedation of patients using anesthesia, which may pose a risk for the patient, requires specialized training for medical personnel, and increases the total procedural cost of the operation for the patient. As such, it may be beneficial to have and use an apparatus capable of treating a bowel impaction that is relatively straightforward to use and capable of maintaining proper sanitary conditions.

As such, to address the challenges associated with the treatment of bowel obstructions, various embodiments of the present invention describe an apparatus and method and/or the like for treating a bowel obstruction with an apparatus.

Figure 1:
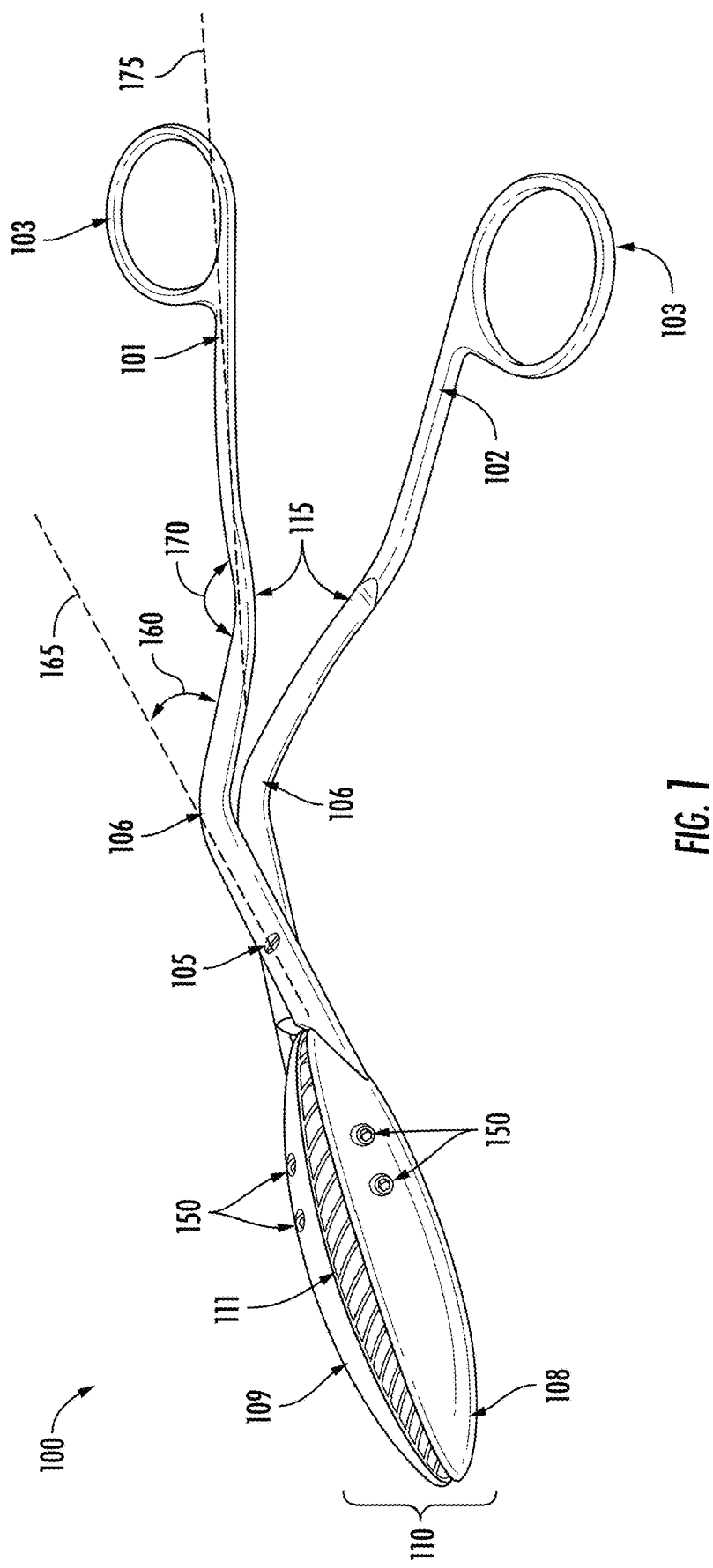
FIG. 1. illustrates an example apparatus configured to treat a bowel impaction in a closed position in accordance with an example embodiment of the present disclosure.

FIG. 1 depicts an apparatus 100 capable of treating a bowel obstruction in accordance with some embodiments of the present invention. The apparatus 100 depicted in FIG. 1 is depicted in a closed position.

Figure 2:
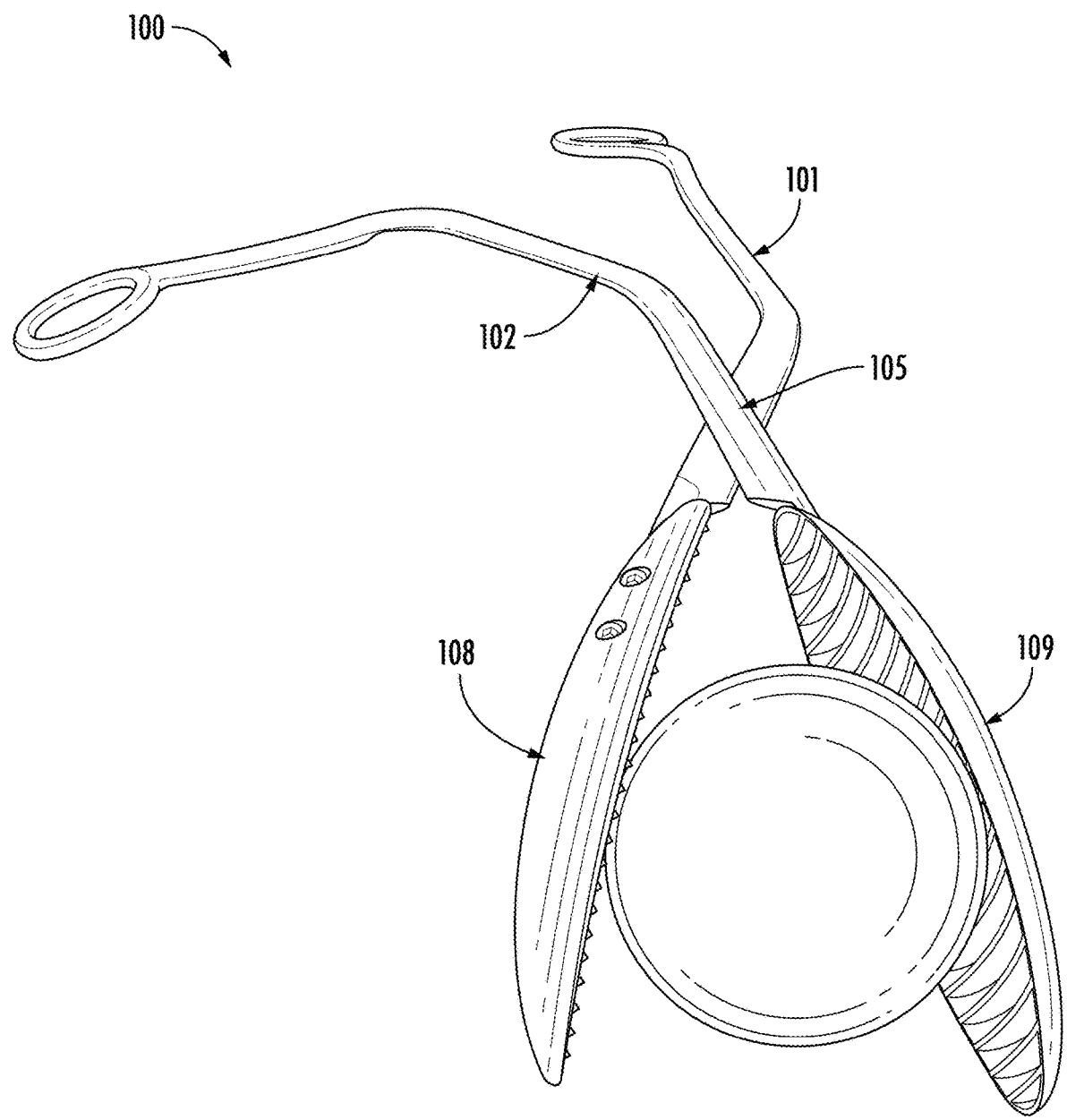
FIG. 2 illustrates an example apparatus in an open position in accordance with an example embodiment of the present disclosure.

The apparatus 100 may include a first tong element 101 and a second tong element 102. The pair of tong elements 101 and 102 may be pivotally connected to enable relative movement between a closed position (e.g., as depicted in FIG. 1) and an open position (e.g., as depicted in FIG. 2), and vice versa. The pair of tong elements 101 and 102 may be pivotally connected at a junction point 105, about which the pair of tong elements 101 and 102 pivot about. In some embodiments, the junction point 105 may be formed using a screw which is threaded through both tong elements 101 and 102. In some embodiment, the pair of tong elements 101 and 102 may be substantially parallel to one another.

Each of the tong elements 101 and 102 may include a proximal end and a distal end and define a body extending therebetween. The proximal end of each tong element 101 and 102 may include a looped handle 103 such that the proximal end of each tong element 101 and 102 may be gripped. In some embodiments, the looped handles 103 may be substantially encased in an encasing material, such as rubber, plastic, and/or the like.

The distal end of first tong element 101 may define a first collection half element 108 and the distal end of the second tong element 102 may define a second collection half element 109. When the pair of tong elements 101 and 102 are in the closed position, the first collection half element 108 and second collection half element 109 may form a collection element 110. The collection element 110 may define an inwardly facing cavity 111. The volume of the cavity 111 defined by collection element 110 may be based at least in part on the distance between the respective interior facing portions of first collection half element 108 and second collection half element 109. In some embodiments, while the pair of tong elements 101 and 102 are in the closed position, the first collection half element 108 and second collection half element 109 form a cone-shape on the distal end of the pair of tong elements 101 and 102.

In some embodiments, the first collection half element 108 and second collection half element 109 are attachable to and removable from the distal end of the first tong element 101 and second tong element 102. In some embodiments, the first collection half element 108 and second collection half element 109 may be attached to the distal end of the first tong element 101 and second tong element 102, respectively, using one or more attachment points 150. In some embodiments, the one or more attachment points 150 are formed by one or more threaded screws which are threaded through the respective collection half element and into the distal portion of the respective tong element. In some embodiments, after use for treatment of a bowel impaction, the first collection half element 108 and second collection half element 109 may be removed and exchanged for new, sanitary first collection half element 108 and second collection half element 109. In some embodiment, the used first collection half element 108 and second collection half element 109 may be sanitized such as by chemical bleaching, ultraviolet radiation, autoclaving, and/or other forms or sterilization.

Once sanitized, the first collection half element 108 and second collection half element 109 may be attached to the apparatus 100 and used again. Additionally or alternatively, in some embodiments, the entire apparatus 100 may be subjected to the aforementioned sanitary procedures.

Furthermore, in some embodiments, the first collection half element 108 and second collection half element 109 may be comprised of a substantially non-porous material. For example, the first collection half element 108 and second collection half element 109 may be a plastic or stainless steel material. As such, the lack of surface porosity further allows for sanitary conditions of the first collection half element 108 and second collection half element 109 to be maintained and/or more easily sanitized.

In some embodiments, the first collection half element 108 and second collection half element 109 may include a distal end and a proximal end, where the proximal end is the end closest to the junction point 105. In some embodiments, the first collection half element 108 and second collection half element 109 may be partially hollow on the proximal end such that the first collection half element 108 and second collection half element 109 may be fitted over a first tong element 101 and second tong element 102. That is, the first tong element 101 and second tong element 102 may be inserted into the opening of the first collection half element 108 and second collection half element 109, respectively, on the proximal end. Once fitted, the first collection half element 108 and/or second collection half element 109 may be securely attached to the first tong element 101 and second tong element 102, respectively, using the one or more attachment points 150.

In some embodiments, each tong element of the pair of tong elements 101 and 102 may define a first bend 106. The first bend 106 may be located on the apparatus body between the junction point 105 and the proximal end of the pair of tong elements 101 and 102. In some embodiments, the first bend 106 is bent such that a first angle 160 is formed for each tong element 101 or 102 when measured from the distal end of the first tong element 101 and/or second tong element 102, as shown by reference line 165. In some embodiments, the first angle 160 inclusively ranges between approximately 5 degrees and 90 degrees. In some embodiments, the first angle 160 is approximately 45 degrees. In some embodiments, the first bend 106 may advantageously allow a medical practitioner to actuate the apparatus 100 and treat a bowel impaction in a more comfortable manner. Additionally, the first bend 106 may provide a medical practitioner with increased freedom to move around a patient and to observe his/her actions from a preferred vantage point. Furthermore, the medical practitioner may have increased control over the various movements, such as insertion and removal, of the apparatus.

In some embodiments, each element of the pair of tong elements 101 and 102 may define a second bend 115. The second bend 115 may be located on the apparatus body between the first bend 106 and the proximal end of the pair of tong elements 101 and 102. In some embodiments, the second bend is bent such that a second angle 170 is formed for each tong element 101 and 102, when measured from the proximal end of the first tong element 101 and/or when measured from the proximal end of the second tong element 102, as shown by reference line 175. In some embodiments, the second angle 170 inclusively ranges between approximately 90 degrees and 175 degrees. In some embodiments, the second angle 170 is approximately 135 degrees. In some embodiments, the second bend 115 may give a medical practitioner additional control during use of the apparatus 100.

In some embodiments, the pair of tong elements 101 and 102 of the apparatus 100 may be substantially straight such that there is the first angle 160 of the first bend 106 and/or second angle 170 of the second bend 115 may be approximately 0 degrees. As such, the pair of tong elements 101 and 102 may be substantially straight in the first bend 106 and/or second bend 115. For certain populations, such as morbidly obese populations, it may be advantageous for the pair of tong elements 101 and 102 to be substantially straight such that the adipose tissue in the buttocks of such populations does not interfere with the apparatus 100 during operation.

With further reference to FIG. 2, depicts the apparatus 100 capable of treating a bowel obstruction in an open position in accordance with some embodiments of the present invention.

In some embodiments, to change configurations between the closed position as depicted in FIG. 1 to the open position depicted in FIG. 2, the proximal ends of the pair of tong elements 101 and 102 may be manually actuated by a user, such as a medical practitioner. To actuate the apparatus 100 from a closed position to an open position, pressure may be applied outwardly such that the proximal ends of the pair of tong elements 101 and 102 move away from one another. As such, this causes the pair of tong elements 101 and 102 to pivot about the junction point 105 and results in the first collection half element 108 and second collection half element 109 separating from one another. In some embodiments, the opening formed by the separation of the first collection half element 108 and second collection half element 109 in at least one separation location may inclusively range between approximately 0.5 centimeters to 10 centimeters. In some embodiments, this separation location may be defined by the maximum distance between the first collection half element 108 and second collection half element 109.

Similarly, to change configurations between the open position to the closed position the proximal ends of the tong elements 101 and 102 may be manually actuated by a user. To actuate the apparatus 100 from an open position to a closed position, pressure may be applied inwardly such that the proximal ends of the pair of tong elements 101 and 102 move toward one another.

Figure 3:
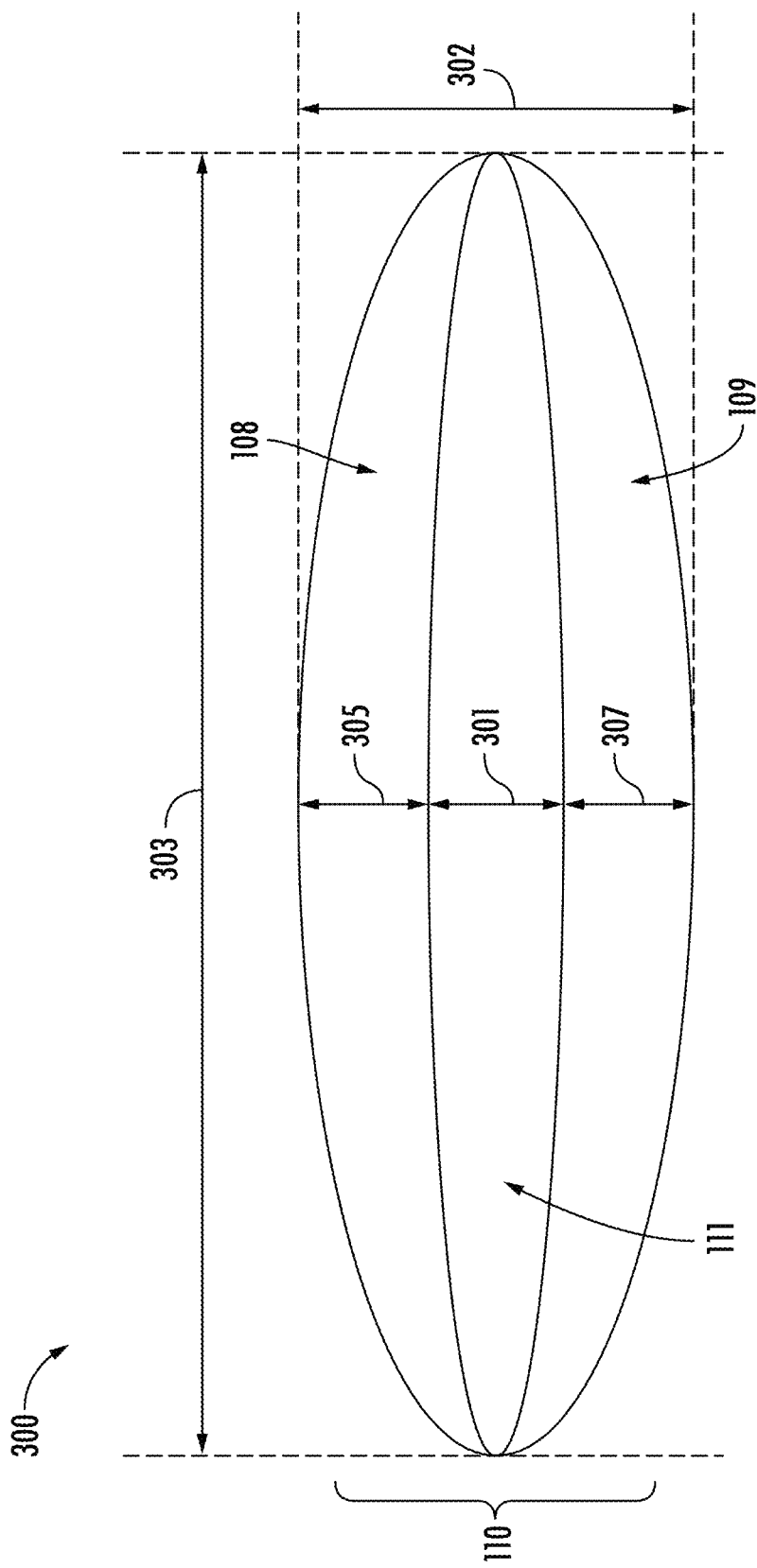
FIG. 3 illustrates a collection element of the apparatus in accordance with an example embodiment of the present disclosure.

Referring now to FIG. 3, the side profile 300 of a collection element 110 formed by the first collection half element 108 and second collection half element 109 of the apparatus 100 is schematically shown. As mentioned above, the collection element 110 is formed by the first collection half element 108 and second collection half element 109 when the apparatus is in the closed position. The collection element may define an inwardly facing cavity. In some embodiments, during treatment of the bowel obstruction, the cavity defined by the collection element 110 may be used to store at least a portion of the bowel obstruction and facilitate removal of the portion of the bowel obstruction from a patient's rectum. In some embodiments, the cavity 111 defined by the collection element 110 may have an associated cavity location height 301 inclusively ranging between in between approximately 0.5 centimeters to 4 centimeters while the pair of tong elements are in the closed position. In some embodiments, this cavity location 301 is defined by the maximum distance between the interior of the first collection half element 108 and the interior of the second collection half element 109.

In some embodiments, the collection element 110 may have an associated length 303 defined based at least in part by a length of the first collection half element 108 and/or second collection half element 109. In some embodiments, the collection element length 303 inclusively ranges between approximately 5 centimeters to 10 centimeters. In some embodiments, the collection element 110 may have an associated width (not shown) defined based at least in part by a width of the first collection half element 108 and/or second collection half element 109. In some embodiments, the width of the collection element 110 ranges inclusively between approximately 2 centimeters to 4 centimeters. In some embodiments, the collection element 110 may have an associated height 302 defined based at least in part by a height of the first collection half element 108 and second collection half element 109. In some embodiments, the collection element height 302 ranges between approximately 2 centimeters to 10 centimeters. However, as will be appreciated by one of skill in the art, a height of the first collection half element 305 and a height of the second collection half element 307 contributes to the width 302 of the collection element 110. The dimensions of the individual collection half elements will be discussed in greater detail with reference to FIG. 4. The associated length and width dimensions of the collection element 110, and by extension, the dimensions of the first collection half element 108 and second collection half element 109 which form the collection element 110, may be based at least in part on the dimensions of the human rectum.

In some embodiments, at least a portion of the collection element 110 is closed such that a portion of the first collection half element 108 and complementary portion of the second collection half element 109 are in contact with one another. Alternatively, in some embodiments, a minimum closed separation distance is defined at any between the first collection half element 108 and second collection half element 109 in the closed position. In some embodiments, the minimum closed separation distance should be approximately 1 millimeter or greater. In some embodiments, the minimum closed separation distance may range approximately between 0.5 centimeters to 1 centimeter. Advantageously, this minimum closed separation distance helps to prevent the accidental enclosure of body tissue between the first collection half element 108 and second collection half element 109 and therefore helps to ensure patient comfort.

Referring now to FIGS. 4A-E, an interior of a collection half element 401 is shown. The collection half element may depict either the first collection half element 108 and/or second collection half element 109. In some embodiments, the interior of the collection half element 401 may be configured with a plurality of grasping teeth 402. In some embodiments, grasping teeth 402 may be located on only one collection half element. In some embodiments, grasping teeth 402 may be located on both the first collection half element and second collection half element. In some embodiments, the inclusion of such grasping teeth may help secure the bowel obstruction within the collection element 110.

Figure 4A:
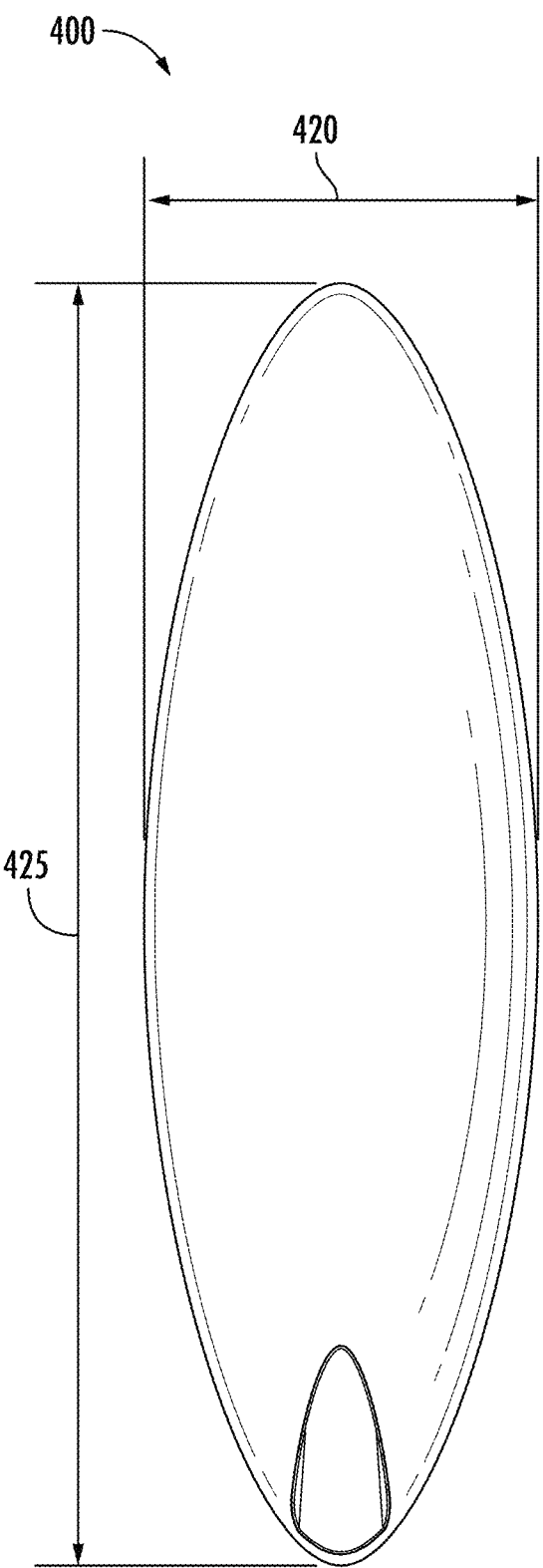
FIGS. 4A-E illustrate various configurations for a plurality of the collection half element and various configuration of grasping teeth according to example embodiments of the present disclosure.

FIG. 4A depicts a top-down representation 400 of a collection half element 401. The collection half element may depict either the first collection half element 108 and/or second collection half element 109. In some embodiments, a length 425 of the collection half element 401 inclusively ranges between approximately 5 centimeters to 10 centimeters. In some embodiments, a width 420 of the collection half element 401 inclusively ranges between approximately 2 centimeters to 4 centimeters. In some embodiments, the associated length 425 and/or width 420 of the first collection half element 108 and second collection half element 109 may be substantially the same.

Figure 4B:
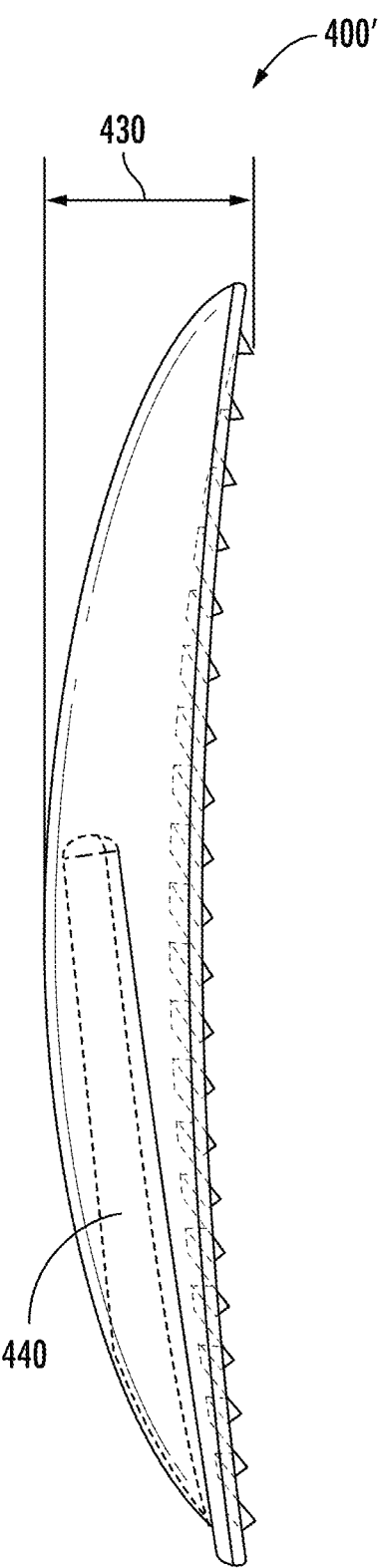

FIG. 4B depicts a side-profile representation 400' of a collection half element 401. In some embodiments, a height 430 of the collection half element 401 inclusively ranges between approximately 0.25 centimeters to 2.5 centimeters. In some embodiments, the associated height 430 of the first collection half element 108 and second collection half element 109 may be substantially the same.

In some embodiments, the collection half element 401 may define a hollow cavity 440. The hollow cavity may be positioned on the proximal end of the collection half element 401 and allow the collection half element 401 to be mated to the corresponding tong element, such as first tong element 108 or second tong element 109. In some embodiments, the hollow cavity 440 has an associated length inclusively ranging between approximately 4 centimeters to 8 centimeters. In some embodiments, the hollow cavity 440 has an associated width inclusively ranging between approximately 0.01 centimeters to 1 centimeter. In some embodiments, the hollow cavity 440 has an associated height inclusively ranging between approximately 0.1 centimeters to 1 centimeter. Once the collection half element 401 is mated with the corresponding tong element, it may be secured using the one or more attachment points.

Figure 4C:
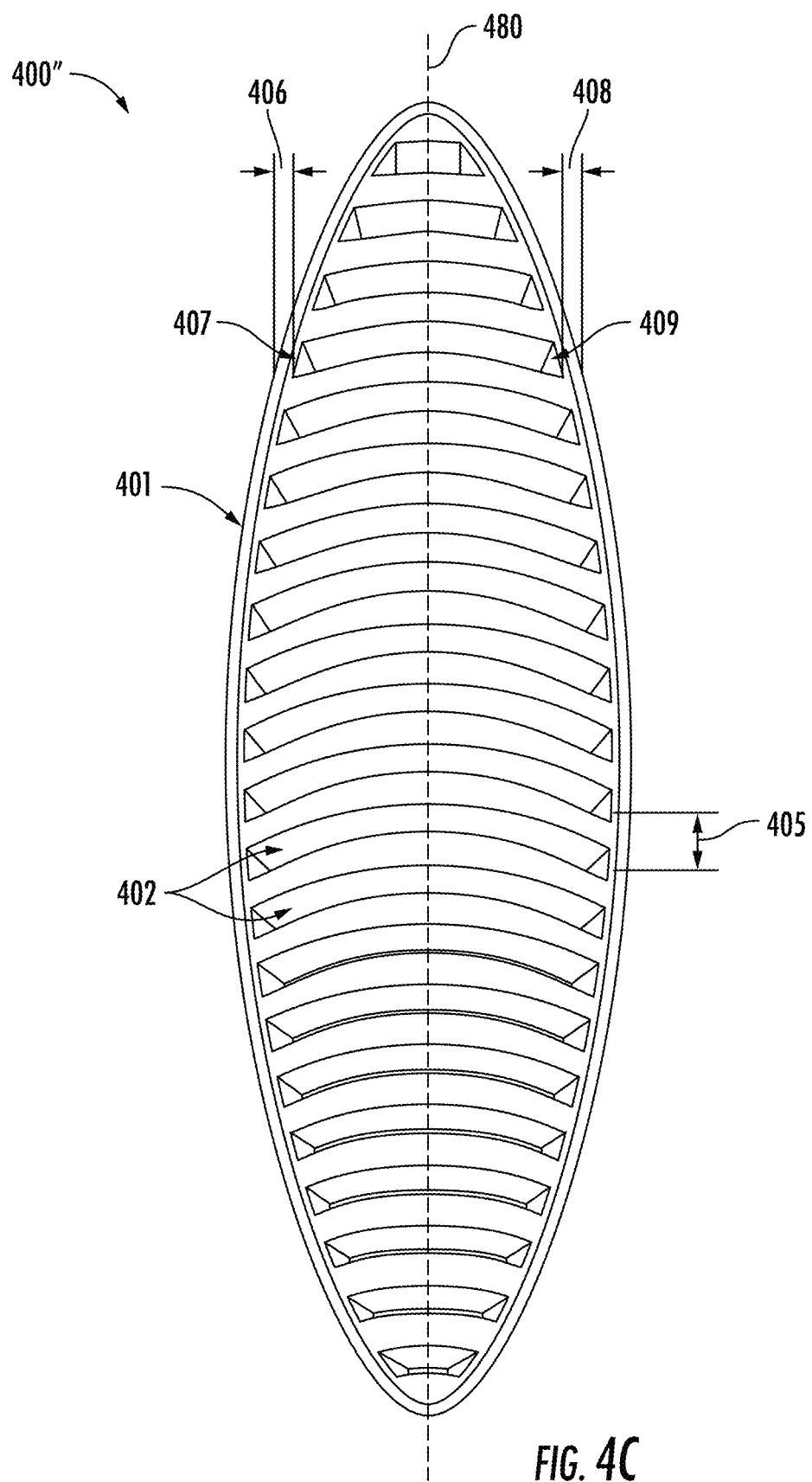

FIG. 4C depicts a configuration of grasping teeth 400" in accordance with an example embodiment. In some embodiments, the plurality of grasping teeth 402 may form a leaved pattern. In some embodiments, the each grasping tooth 402 is substantially parabolic in shape and spans horizontally across the interior of the collection half element 401. In some embodiments, each grasping tooth 402 may span a portion of the interior of the collection half element 401 defined by a first gap 406 and second gap 408. The first gap 406 may be defined by the space between an adjacent external edge of the collection half element 401 and a first end of the grasping tooth 407. The second gap 408 may be defined by the space between an adjacent external edge of the collection half element 401 and a second end of the grasping tooth 409. The adjacent external edge of the collection half element 401 may be the point on the collection half element that is within the closest proximity to the grasping tooth end of interest. In some embodiments, the first gap 406 may inclusively range between approximately 0.5 millimeters to 10 millimeters. In some embodiments, the second gap 408 may inclusively range between approximately 0.5 millimeters to 10 millimeters. In some embodiments, the plurality of grasping teeth 402 may be defined by substantially the same first gap 406 and second gap 408 such that the central point of the plurality of grasping teeth 402 are substantially aligned with one another. In some embodiments, the central point of the plurality of grasping teeth 402 may aligned with a reference line 480, which may bisect the collection half element 401 lengthwise.

In some embodiments, a distance 405 between one or more grasping teeth of the plurality of grasping teeth 402 may inclusively range from approximately between 0.1 centimeters to 5 centimeters. In some embodiments, the distance 405 between each of the one or more adjacent grasping teeth may be substantially the same. In some embodiments, the distance 405 between each of the one or more adjacent grasping teeth may be different.

Figure 4D:
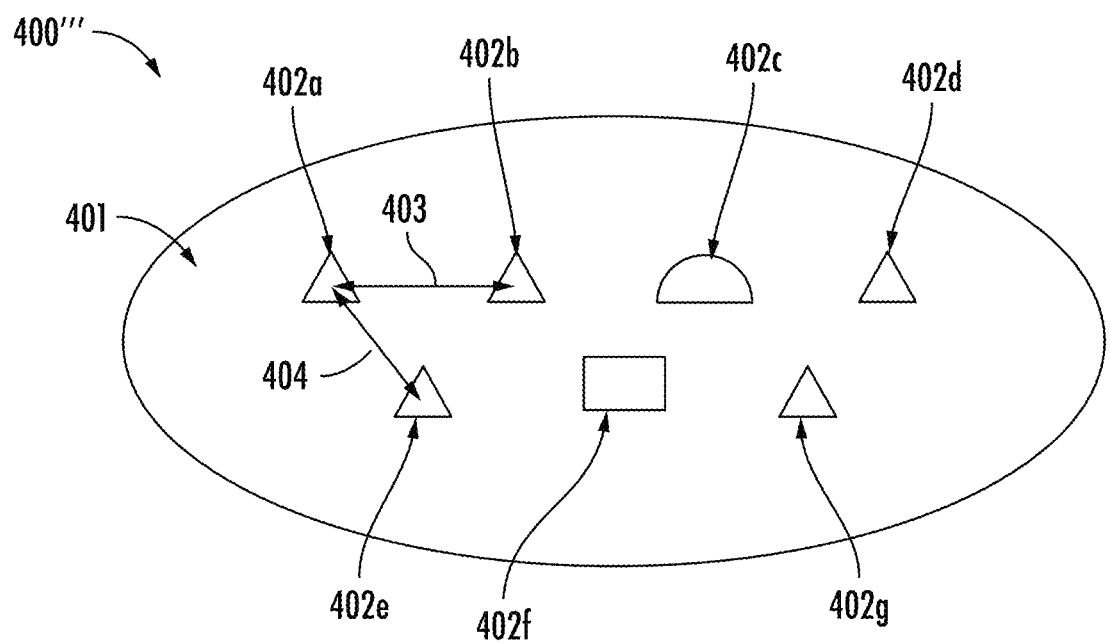

FIG. 4D depicts a configuration of grasping teeth 400' in accordance with an example embodiment. In some embodiments, the plurality of grasping teeth 402a-402g may be substantially round, rectangular, conical, pyramidal, and/or the like in shape. In some embodiments, the plurality of grasping teeth 402a-402g may include any combination of shapes. For example, grasping tooth 402a may be pyramidal in shape, grasping tooth 402c may be round in shape, and grasping tooth 402f may be rectangular in shape.

In some embodiments, plurality of grasping teeth 402a-402g located on a particular collection half element (e.g., first collection half element 108 and/or second collection half element 109) may be spaced equidistantly from one another. For example, the distance 403 between a grasping tooth 402a and a grasping tooth 402b is the same as the distance 404 between the grasping tooth 402a and a grasping tooth 402e. Although FIG. 4A shows distances 403 and 404 measured from the center of each grasping tooth, any spot on the grasping tooth may be selected to serve a measuring point. In some embodiments, the distance between two or more grasping teeth may inclusively range from approximately 0.1 centimeters to 5 centimeters.

In some embodiments, the length of a grasping tooth may extend outwardly from the interior of a first collection half element 108 and/or a second collection half element 109. In some embodiments, the length of a grasping tooth may inclusively range between approximately 0.5 millimeters to 10 millimeters. Alternatively, one or more grasping teeth of the plurality of grasping teeth 402a-402g may be a different length than one or more other grasping teeth. In some embodiments, each grasping teeth may be of the same length. In some embodiments, one or more grasping teeth of the plurality of grasping teeth 402a-402g may be angled. In some embodiments, the one or more grasping teeth may be angled backward towards the proximal end of the first collection half element 108 and/or second collection half element 109. The angled teeth may help to secure the bowel obstruction during operation.

Figure 4E:
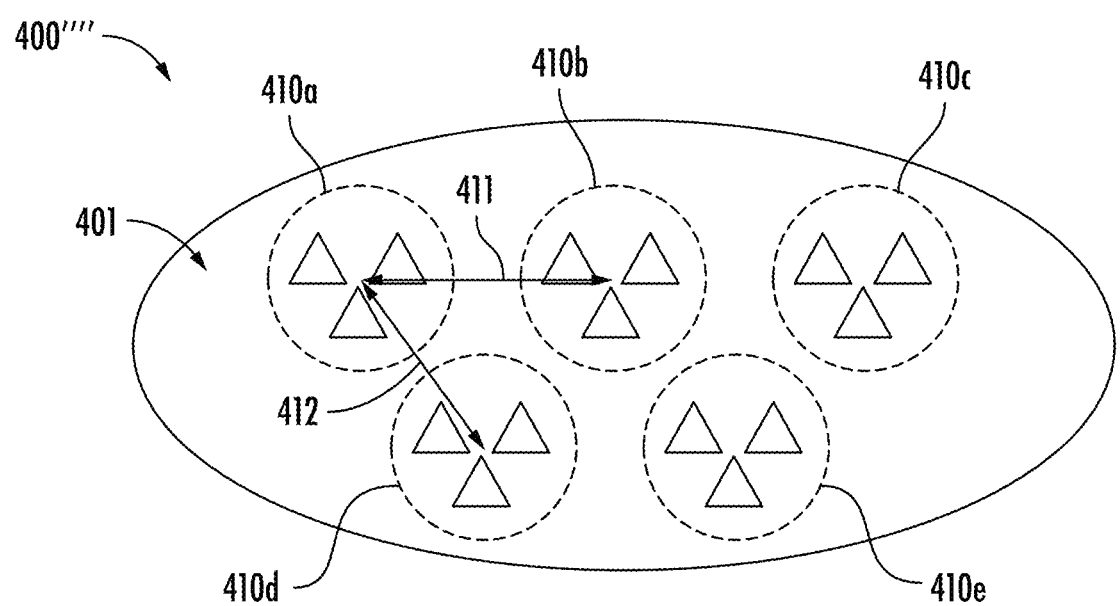

Referring now to FIG. 4E, another configuration of grasping teeth 400"" is depicted in accordance with an example embodiment. In some embodiments, the plurality of grasping teeth may include grasping teeth sub-groups 410a-e. Each grasping teeth sub-group may include one or more grasping teeth. For example, grasping teeth sub-group 410a includes three grasping teeth. In some embodiments, each grasping teeth sub-group may include the same number of grasping teeth. Alternatively, grasping teeth sub-groups may include a different number of grasping teeth than other grasping teeth sub-groups.

In some embodiments, the grasping teeth sub-groups 410a-e may be located equidistantly from one another. For example, the distance 411 between a grasping teeth sub-group 410a and a grasping teeth sub-group 410b is the same as the distance 412 between the grasping teeth sub-group 410a and a grasping teeth sub-group 410d. Although FIG. 4A shows distances 411 and 412 measured from the center of each grasping tooth sub-group, any spot of the grasping tooth sub-group may be selected to serve a measuring point. In some embodiments, the distance between two or more grasping teeth subgroups may inclusively range from approximately 0.1 centimeters to 5 centimeters.

Figure 5A:
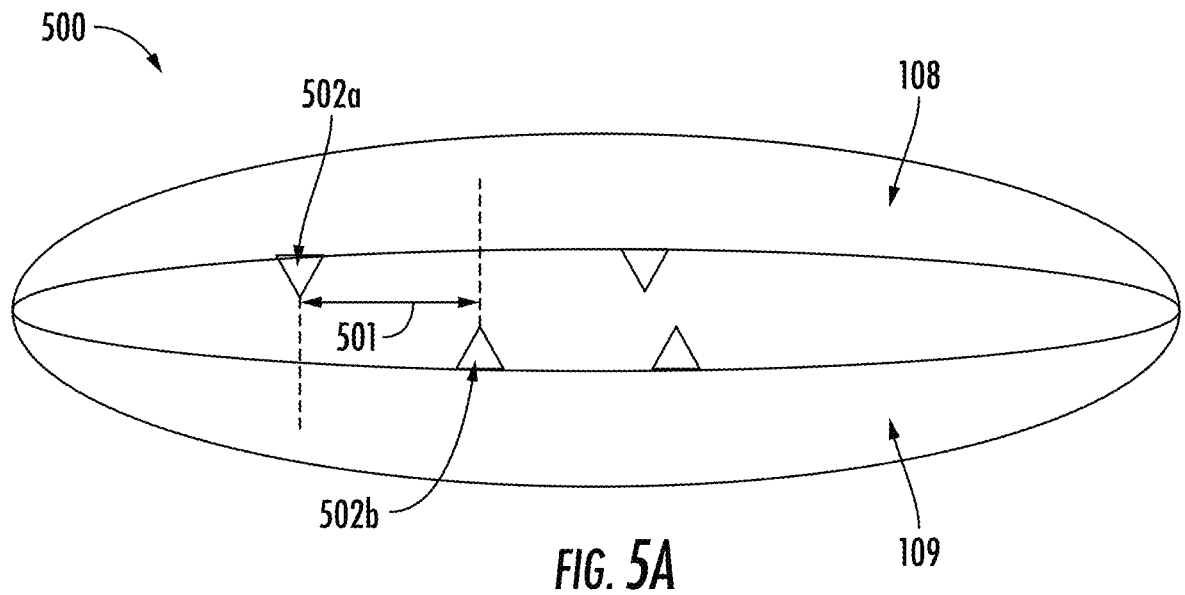
FIGS. 5A-B illustrates various alignments for a plurality of grasping teeth according to example embodiments of the present disclosure.
Figure 5B:
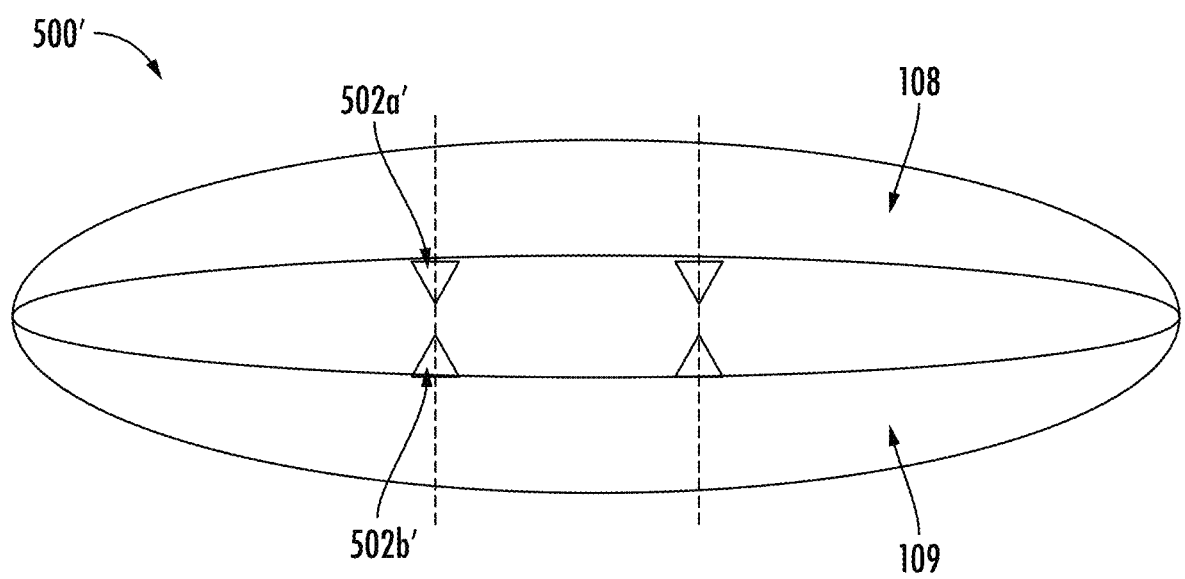

Referring now to FIGS. 5A-B, a grasping teeth configuration 500 between the first collection half element 108 and second collection half element 109 in accordance with some example embodiments are depicted.

As depicted in FIG. 5A, a grasping teeth configuration 500 may be such that one or more grasping teeth of the first collection half element 108 are offset from one or more grasping teeth of the second collection half element 109. In some embodiments, the one or more grasping teeth may be offset by an offset distance 501. In some embodiments, the offset distance 501 between the one or more a grasping tooth 502a of the first collection half element 108 and a grasping tooth 502b of the second collection half element 109 may inclusively range between approximately 0.05 centimeters to 1 centimeter. In some embodiments, the distance between one or more grasping teeth of the first collection half element 108 and one or more grasping teeth of the second collection half element 109 may be different from the distance between one or more other grasping teeth of the first collection half element 108 and one or more other grasping teeth of the second collection half element 109.

As depicted in FIG. 5B, a grasping teeth configuration 500' may be such that one or more grasping teeth of the first collection half element 108 are aligned with one or more grasping teeth of the second collection half element 109. For example, a grasping tooth 502a' of the first collection half element 108 may be substantially aligned with a grasping tooth 502b' of the second collection half element 109.

In some embodiments, a grasping teeth configuration may include both grasping teeth of a collection half element offset from grasping teeth of a corresponding collection half element and grasping teeth of a collection half element which are aligned with grasping teeth of a corresponding collection half element.

Figure 6:
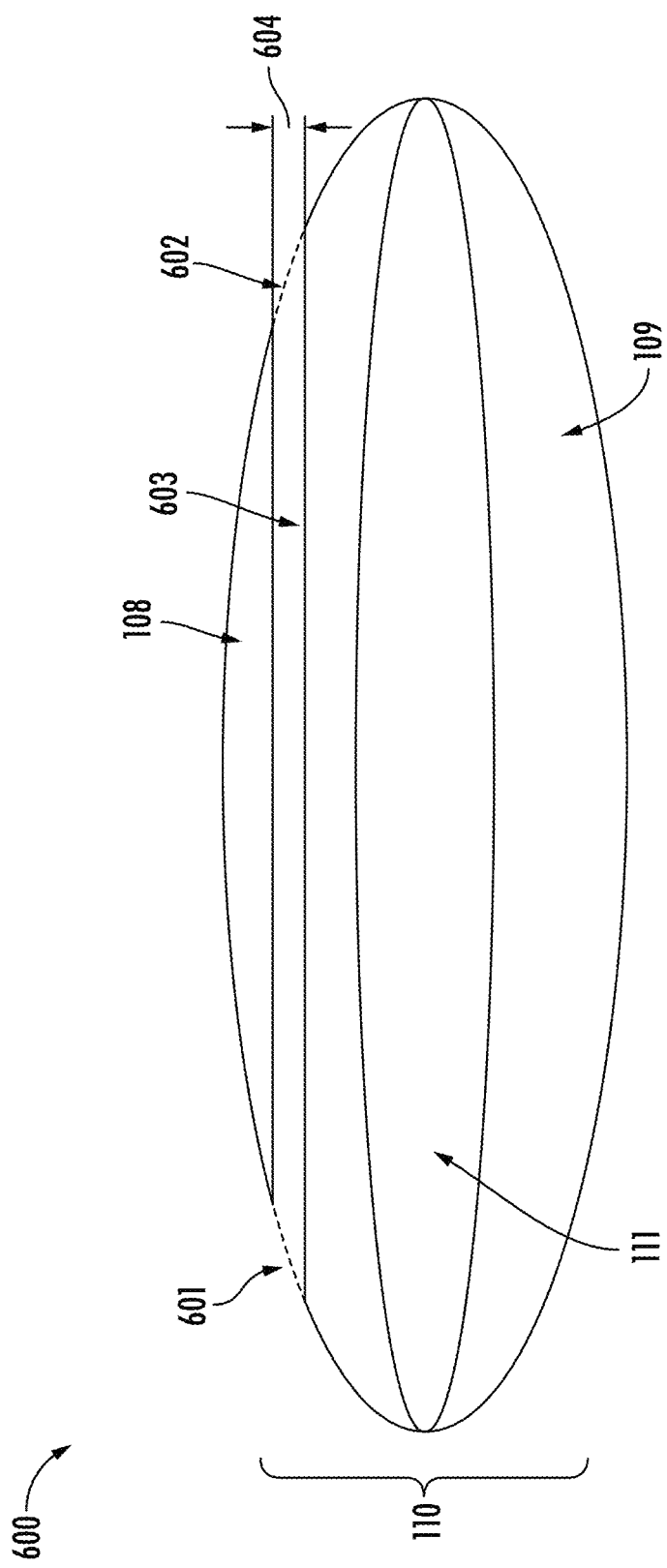
FIG. 6 illustrates a cross-section of an apparatus configured with a port.

In some embodiments, the first collection half element 108 and/or second collection half element 109 may define one or more ports. As depicted in FIG. 6, a cross-sectional view of an apparatus 600 with a first collection half element 108 configured with a port 603. The port 603 may span across the interior of the collection half element from a first end 601 to a second end 602. In some embodiments, the diameter of the port 604 may range between 0.2 centimeters to 2 centimeters. The one or more ports may allow for the insertion of one or more aiding tools to be inserted into a patient rectum substantially with the apparatus 100. For example, the one or more aiding tools may include a three-prong extraction device, a light source, a Boor scope camera, a saline irrigation pump, and/or the like. As will be appreciated by one of skill in the art, although a single port 603 is depicted within a first collection half element 108, the second collection half element 109 may additionally or alternatively be configured with a port and each collection half element may define one or more ports.

Figure 7:
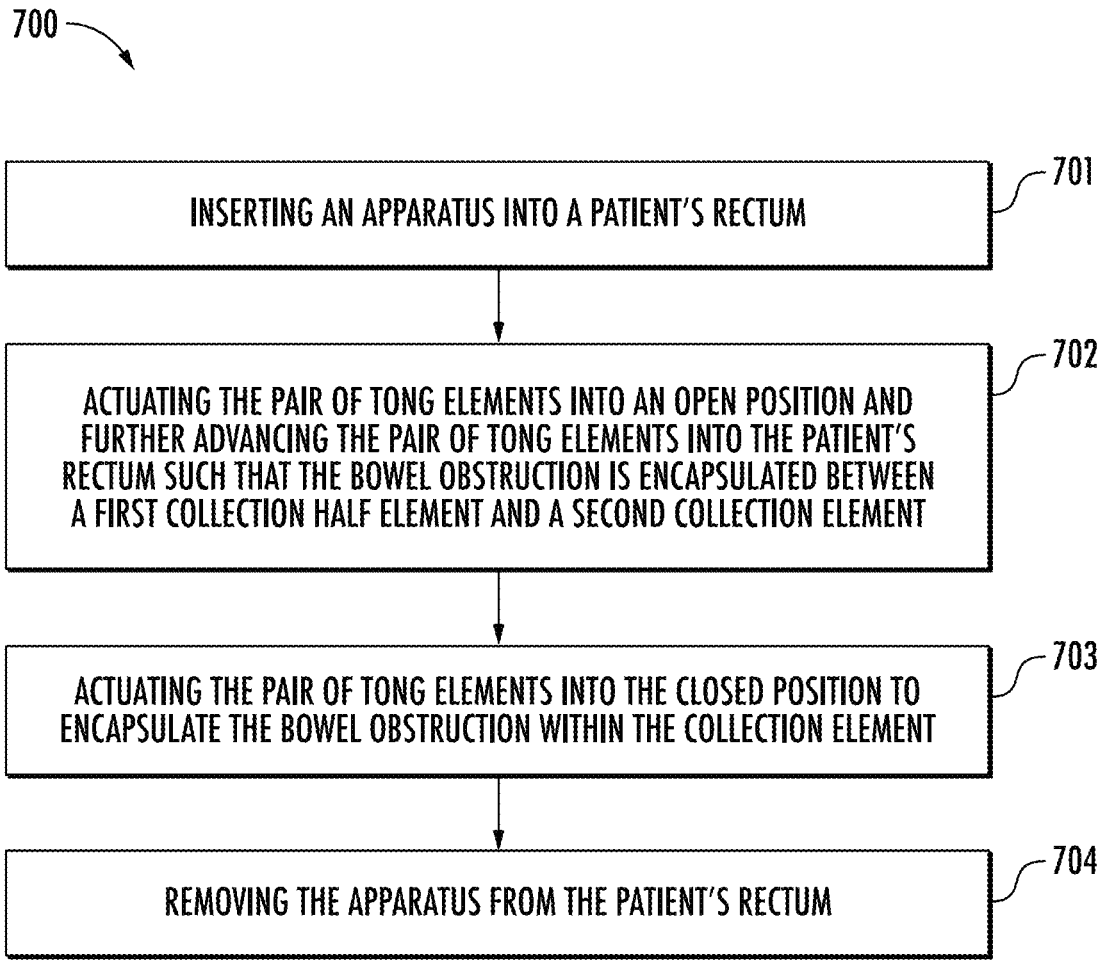
FIG. 7 is a flowchart of a method for treatment of a bowel impaction according to an example embodiment of the present disclosure.

FIG. 7 shows a flowchart 700 depicting an example process of the present invention. In particular, FIG. 7 describes an example method for treating a bowel impaction.

The method may begin at step/operation 701, wherein an apparatus is inserted into a patient's rectum. In some embodiments, the apparatus may be the apparatus 100 as described above in accordance with any of the embodiments as described above. In some embodiments, prior to insertion of the apparatus, a lubricant may be disposed on the outside surface of the first collection half element 108 and second collection half element 109. In some embodiments, the apparatus 100 is inserted into the patient's rectum while in the closed position. In some embodiments, only the first collection half element 108 and second collection half element 109 are inserted into the patient's rectum. In some embodiments, only a portion of the first collection half element 108 and a portion of the second collection half element 109 are inserted into the patient's rectum.

At step/operation 702, the pair of tong elements 101 and 102 may be actuated into an opened position and further advanced into the patient's rectum such that at least a portion of the bowel obstruction is encapsulated between the first collection half element 108 and second collection half element 109. To actuate the apparatus 100 from a closed position to an open position, pressure may be applied outwardly on the proximal ends of the apparatus such that the proximal ends of the pair of tong elements 101 and 102 move away from one another.

At step/operation 703, the pair of tong elements 101 and 102 may be actuated into the closed position to encapsulate at least a portion of the bowel obstruction within the collection element 110. To actuate the apparatus 100 from an open position to a closed position, pressure may be applied inwardly on the proximal ends of the apparatus 100 such that the proximal ends of the pair of tong elements 101 and 102 move towards each other.

At step/operation 704, the apparatus 100 is removed from the patient's rectum. Any bowel obstruction that was removed from the patient's rectum may then be disposed of. As such, a bowel impaction may be removed from the patient using apparatus 100 such that the patient is successfully treated.

As will be appreciated by one of skill in the art, although the example apparatus and method is discussed for treatment of a bowel impaction, the described apparatus and method may also be used to treat a variety of other conditions. For example, the described apparatus and/or method may be used to for anal foreign body extraction, vaginal foreign body extractions, fecal transplantation and/or the like.

The invention has been described in detail with particular reference to preferred embodiments and the use thereof. There are many possible modifications and embodiments that one skilled in the art could apply. Therefore, it is to be understood that this disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. An apparatus configured to treat a bowel impaction, the apparatus comprising:
    a first tong element and a second tong element forming a pair of tong elements, the pair of tong elements pivotally connected at a junction point and movable between an opened position and a closed position;
    each tong element defining a distal end and a proximal end and a body extending therebetween; and
    the distal end of the first tong element defining a first collection half element and the distal end of the second tong element defining a second collection half element, wherein (i) the first collection half element and the second collection half element form a collection element when the pair of tong elements are in the closed position, (ii) the collection element defining an inwardly facing cavity, (iii) a plurality of grasping teeth are defined on both an interior of the first collection half element and an interior of the second collection half element, and (iv) each of the plurality of grasping teeth is angled backward towards the junction point such that for each grasping tooth of the plurality of grasping teeth, a distal end oriented surface of the grasping tooth is larger than a proximal end oriented surface of the grasping tooth,
    wherein the plurality of grasping teeth define laterally extending substantially parabolic shapes that span across the interior of the first collection half element or the second collection half element, wherein the laterally extending substantially parabolic shape of a first tooth of the plurality of grasping teeth is positioned distally adjacent to the laterally extending substantially parabolic shape of a second tooth of the plurality of grasping teeth defining a laterally extending substantially parabolic gap between a proximal base of the first tooth of the plurality of grasping teeth and a distal base of the second tooth of the plurality of grasping teeth, and wherein each grasping tooth of the plurality of grasping teeth defines a laterally extending substantially parabolic grasping edge between the proximal end oriented surface and the distal end oriented surface.

2. The apparatus of claim 1, the apparatus further comprising:

each tong element defining a first bend and a second bend each located on the respective tong element body between the junction point and proximal end of the respective tong element, wherein the first bend forms a first obtuse angle on the respective tong element body and the second bend forms a second obtuse angle on the respective tong element body.

3. The apparatus of claim 1, wherein the first collection half element is removably attached to the distal end of the first tong element and the second collection half element is removably attached to the distal end of the second tong element.

4. The apparatus of claim 1, wherein:
the plurality of grasping teeth on each respective collection half element are located equidistantly from one another.

5. The apparatus of claim 1, wherein:
the plurality of grasping teeth on each respective collection half element are offset by an offset distance from the plurality of grasping teeth on the opposing collection half element.

6. The apparatus of claim 1, wherein:
the plurality of grasping teeth on each respective collection half element are aligned with the plurality of grasping teeth on the opposing collection half element.

7. The apparatus of claim 1, wherein a length of the plurality of grasping teeth as measured from the respective collection half interior surface to a maximum grasping teeth height inclusively ranges between approximately 0.5 millimeters to 10 millimeters.

8. The apparatus of claim 1, wherein the first collection half element and second collection half element form a cone-shape when the pair of tong elements are in the closed position.

9. The apparatus of claim 1, wherein the inwardly facing cavity defined by the collection element includes at least one cavity location defined by a height inclusively ranging between approximately 0.5 centimeter to 4 centimeters while the pair of tong elements are in the closed position.

10. The apparatus of claim 1, wherein a height of the collection element defined by a height of both the first collection half element and a height of the second collection half element inclusively ranges between approximately 2 centimeters to 10 centimeters.

11. The apparatus of claim 1, wherein a length of the collection element defined by a length of the first collection half element or a length of the second collection half element inclusively ranges between approximately 5 centimeters to 10 centimeters.

12. The apparatus of claim 1, wherein the first collection half element and the second collection half element each comprise a substantially non-porous material.

13. The apparatus of claim 1, wherein the laterally extending substantially parabolic grasping edge defines a concavity directed towards the proximal end.

14. The apparatus of claim 13, wherein the laterally extending substantially parabolic grasping edge of the first tooth is positioned closer to the laterally extending substantially parabolic gap than the laterally extending substantially parabolic grasping edge of the second tooth is to the laterally extending substantially parabolic gap.

15. A method for treatment of a bowel impaction, the method comprising:

inserting an apparatus into a patient's rectum, said apparatus comprising:

a first tong element and a second tong element forming a pair of tong elements, the pair of tong elements pivotally connected at a junction point and movable between an opened position and a closed position;

each tong element defining a distal end and a proximal end and a body extending therebetween; and the distal end of the first tong element defining a first collection half element and the distal end of the second tong element defining a second collection half element, wherein (i) the first collection half element and the second collection half element form a collection element when the pair of tong elements are in the closed position, (ii) the collection element defining an inwardly facing cavity, (iii) a plurality of grasping teeth are defined on both an interior of the first collection half element and an interior of the second collection half element, and (iv) each of the plurality of grasping teeth is angled backward towards the junction point such that for each grasping tooth of the plurality of grasping teeth, a distal end oriented surface of the grasping tooth is larger than a proximal end oriented surface of the grasping tooth, wherein the plurality of grasping teeth define laterally extending substantially parabolic shapes that span across the interior of the first collection half element or the second collection half element, wherein the laterally extending substantially parabolic shape of a first tooth of the plurality of grasping teeth is positioned distally adjacent to the laterally extending substantially parabolic shape of a second tooth of the plurality of grasping teeth defining a laterally extending substantially parabolic gap between a proximal base of the first tooth of the plurality of grasping teeth and a distal base of the second tooth of the plurality of grasping teeth, and wherein each grasping tooth of the plurality of grasping teeth defines a laterally extending substantially parabolic grasping edge between the proximal end oriented surface and the distal end oriented surface;

actuating the pair of tong elements into the opened position and further advancing the pair of tong elements into the patient's rectum such that at least a portion of the bowel impaction is encapsulated between the first collection half element and the second collection half element;

actuating the pair of tong elements into the closed position to encapsulate at least a portion of the bowel impaction within the collection element; and removing the apparatus from the patient's rectum.

16. The method of claim 15, wherein a lubricant is disposed on the outside surface of the first collection half element and the second collection half element prior to insertion of the apparatus into the patient's rectum.

17. The method of claim 15, wherein only the first collection half element and the second collection half element are inserted into the patient's rectum.

* * * * *